United States Patent
Liu et al.

(10) Patent No.: US 7,435,084 B2
(45) Date of Patent: *Oct. 14, 2008

(54) SYSTEM AND METHODS FOR CASTING PHYSICAL TOOTH MODEL

(75) Inventors: Frank Zhenhuan Liu, Redwood City, CA (US); Huafeng Wen, Redwood City, CA (US)

(73) Assignee: Align Technology, Inc., Santa Clara, CA (US)

( * ) Notice: Subject to any disclaimer, the term of this patent is extended or adjusted under 35 U.S.C. 154(b) by 422 days.

This patent is subject to a terminal disclaimer.

(21) Appl. No.: 11/013,160

(22) Filed: Dec. 14, 2004

(65) Prior Publication Data

US 2006/0127838 A1    Jun. 15, 2006

(51) Int. Cl.
*A61C 9/00* (2006.01)

(52) U.S. Cl. ........................................................ 433/34

(58) Field of Classification Search .................. 433/34, 433/35, 36, 213
See application file for complete search history.

(56) References Cited

U.S. PATENT DOCUMENTS

| 3,636,632 | A * | 1/1972 | Costa et al. ................. 433/213 |
| 6,386,865 | B1 * | 5/2002 | Suh et al. ....................... 433/27 |
| 6,913,462 | B2 * | 7/2005 | Honstein et al. .............. 433/57 |
| 7,048,031 | B2 * | 5/2006 | Usui ............................ 164/335 |
| 2004/0023185 | A1 * | 2/2004 | Gittleman .................... 433/34 |

* cited by examiner

*Primary Examiner*—Melba Bumgarner
(74) *Attorney, Agent, or Firm*—Paul, Hastings, Janofsky & Walker LLP

(57) ABSTRACT

A casting chamber for casting a physical tooth model representing a patient's tooth includes a chamber body and a lid. The chamber body includes a cavity adapted to hold a negative impression of the patient's tooth and to receive a cast material, wherein the negative impression and the chamber body are registered by a registration unit. The chamber lid is configured to seal the cast material in the casting chamber to permit the casting material to solidify in the casting chamber to form a physical tooth model representing the patient's tooth.

29 Claims, 12 Drawing Sheets

310  330

315  320

SYSTEM AND METHODS FOR CASTING PHYSICAL TOOTH MODEL

TECHNICAL FIELD

This application generally relates to the field of dental care, and more particularly to a system and a method for manufacturing and constructing a physical dental arch model.

CROSS-REFERENCES TO RELATED INVENTIONS

The present invention is related to concurrently filed and commonly assigned U.S. patent application, titled "A base for physical dental arch model" by Huafeng Wen, concurrently filed and commonly assigned U.S. patent application, titled "Accurately producing a base for physical dental arch model" by Huafeng Wen, concurrently filed and commonly assigned U.S. patent application, titled "Fabricating a base compatible with physical dental tooth models" by Huafeng Wen, concurrently filed and commonly assigned U.S. patent application, titled "Producing non-interfering tooth models on a base" by Huafeng Wen, concurrently filed and commonly assigned U.S. patent application, titled "Producing a base for accurately receiving dental tooth models" by Huafeng Wen, and concurrently filed and commonly assigned U.S. Patent Application, titled "Producing accurate base for dental arch model" by Huafeng Wen.

The present invention is also related to U.S. Patent Application, titled "Method and apparatus for manufacturing and constructing a physical dental arch model" by Huafeng Wen, Nov. 1, 2004, U.S. Patent Application, titled "Method and apparatus for manufacturing and constructing a dental aligner" by Huafeng Wen, Nov. 1, 2004, U.S. Patent application, titled "Producing an adjustable physical dental arch model" by Huafeng Wen, Nov. 1, 2004, and U.S. Patent Application, titled "Producing a base for physical dental arch model" by Huafeng Wen, Nov. 1, 2004. The disclosure of these related applications are incorporated herein by reference.

BACKGROUND

Orthodontics is the practice of manipulating a patient's teeth to provide better function and appearance. In general, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

In general, the orthodontist makes manual adjustments to the wire and/or replaces or repositions brackets based on his or her expert opinion. Unfortunately, in the oral environment, it is impossible for a human being to accurately develop a visual three-dimensional image of an orthodontic structure due to the limitations of human sight and the physical structure of a human mouth. In addition, it is humanly impossible to accurately estimate three-dimensional wire bends (with an accuracy within a few degrees) and to manually apply such bends to a wire. Further, it is humanly impossible to determine an ideal bracket location to achieve the desired orthodontic structure based on the mental images. It is also extremely difficult to manually place brackets in what is estimated to be the ideal location. Accordingly, orthodontic treatment is an iterative process requiring multiple wire changes, with the process success and speed being very much dependent on the orthodontist's motor skills and diagnostic expertise. As a result of multiple wire changes, patient discomfort is increased as well as the cost. As one would expect, the quality of care varies greatly from orthodontist to orthodontist as does the time to treat a patient.

As described, the practice of orthodontic is very much an art, relying on the expert opinions and judgments of the orthodontist. In an effort to shift the practice of orthodontic from an art to a science, many innovations have been developed. For example, U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Kuroda et al. (1996) Am. J. Orthodontics 110:365-369 describes a method for laser scanning a plaster dental cast to produce a digital image of the cast. See also U.S. Pat. No. 5,605,459. U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912.Computerized digital imaging of the arch is described in U.S. Pat. Nos. 5,342,202 and 5,340,309.

Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

The key to efficiency in treatment and maximum quality in results is a realistic simulation of the treatment process. Today's orthodontists have the possibility of taking plaster models of the upper and lower arch, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per arch that covers all brackets and relevant portions of every tooth. Using such a transfer tray guarantees a very quick and yet precise bonding using indirect bonding.

U.S. Pat. No. 5,431,562 to Andreiko et al. describes a computerized, appliance-driven approach to orthodontics. In this method, first certain shape information of teeth is acquired. A uniplanar target arcform is calculated from the shape information. The shape of customized bracket slots, the bracket base, and the shape of the orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

More recently, Align Technology, Inc. began offering transparent, removable aligning devices as a new treatment modality in orthodontics. In this system, an impression model of the dentition of the patient is obtained by the orthodontist and shipped to a remote appliance manufacturing center, where it is scanned with a CT scanner. A computer model of the dentition in a target situation is generated at the appliance manufacturing center and made available for viewing to the orthodontist over the Internet. The orthodontist indicates changes they wish to make to individual tooth positions. A revised virtual model is provided for the orthodontist to review, until the target situation is agreed upon. A series of removable aligning devices or shells are manufactured and delivered to the orthodontist. The shells will move the patient's teeth to the desired or target position.

U.S. Pat. No. 6,699,037 describes improved methods and systems for repositioning teeth from an initial tooth arrangement to a final tooth arrangement. Repositioning is accomplished with a system comprising a series of appliances configured to receive the teeth in a cavity and incrementally reposition individual teeth in a series of successive steps, usually including at least four successive steps, often including at least ten steps, sometimes including at least twenty-five steps, and occasionally including forty or more steps. Most often, the methods and systems will reposition teeth in from ten to twenty-five successive steps, although complex cases involving many of the patient's teeth may take forty or more steps. The successive use of a number of such appliances permits each appliance to be configured to move individual teeth in small increments, typically less than 2 mm, preferably less than 1 mm, and more preferably less than 0.5 mm. These values refer to the maximum linear translation of any point on a tooth as a result of using a single appliance. The movements provided by successive appliances, of course, will usually not be the same for any particular tooth. Thus, one point on a tooth may be moved by a different distance as a result of the use of one appliance and thereafter moved by a different distance and/or in a different direction by a later appliance.

The individual appliances preferably comprise a polymeric shell having the teeth-receiving cavity formed therein, typically by molding. Each individual appliance is configured so that its tooth-receiving cavity has a geometry corresponding to an intermediate or end tooth arrangement intended for that appliance. That is, when an appliance is first worn by the patient, certain of the teeth will be misaligned relative to an undeformed geometry of the appliance cavity. The appliance, however, is sufficiently resilient to accommodate or conform to the misaligned teeth, and will apply sufficient resilient force against such misaligned teeth in order to reposition the teeth to the intermediate or end arrangement desired for that treatment step.

The fabrication of aligners using a stereo lithography process is disclosed in U.S. Pat. Nos. 6,471,511 and 6,682,346. The stereo lithography process builds the aligner layer by layer, and may use a different aligner mold at each stage of the treatment.

The practice of orthodontics and other dental treatments including preparation of a denture can benefit from a physical dental arch model that is representative of the dentition and the alveolar ridge of a patient to be orthodontically treated. The physical dental arch model, also referred as a physical dental arch model, is often prepared based on an impression model. The physical dental arch model is generally prepared by cutting and arranging individual teeth on the alveolar ridge of the impression model. With this physical dental arch model so prepared, not only is a final goal for the dental treatment made clear, but also the occlusal condition between the maxillary and the mandibular dentitions can be ascertained specifically.

Also, the patient when the physical dental arch model is presented can visually ascertain the possible final result of orthodontic treatment he or she will receive and, therefore, the physical dental arch model is a convenient tool in terms of psychological aspects of the patient.

Making a model for a whole or a large portion of an arch is more difficult than making one tooth abutment for implant purposes. Single teeth do not have concavities and complexities as in the inter-proximal areas of teeth in an arch. Some prior art making the physical dental arch model is carried out manually, involving not only a substantial amount of labor required, but also a substantial amount of time. It is also difficult to machine an accurate arch model because of the various complex shapes and the complex features such as inter-proximal areas, wedges between teeth, among others, in an arch.

SUMMARY OF THE INVENTION

In one aspect, the present system relates to a casting chamber for casting a physical tooth model representing a patient's tooth, comprising:

a chamber body having a cavity adapted to hold the negative impression of the patient's tooth and to receive a cast material; and a chamber lid configured to seal the cast material in the casting chamber to permit the casting material to solidify in the casting chamber thereby forming a physical tooth model representing the patient's tooth.

In another aspect, the present system relates to a casting chamber for casting a physical tooth model representing a patient's tooth, comprising:

a chamber body having a cavity adapted to hold the negative impression of the patient's tooth and to receive a cast material and chamber walls surrounding the cavity, wherein the negative impression and the chamber body are registered by a registration unit; and a chamber lid configured to seal the cast material in the casting chamber to permit the casting material to solidify in the casting chamber thereby forming a physical tooth model representing the patient's tooth.

In yet another aspect, the present system relates to a method for producing a physical tooth model, comprising:

holding a negative impression of a patient's tooth in a casting chamber by a registration unit;

pouring a cast material over the negative impression of the patient's tooth; and solidifying the cast material to produce the physical tooth model.

Embodiments may include one or more of the following advantages. An advantage of the present system is that the physical tooth models can be produced with simple, inexpensive and reliable methods and system. The physical tooth models are molded to the correct shape including features to allow them to be inserted, attached, or plugged to a dental base. The physical tooth models can be pre-fabricated having standard registration and attaching features for assembling. The physical tooth models can be automatically assembled onto a base by a robotic arm under computer control. The manufacturable components can be attached to a base. The assembled physical dental arch model specifically corresponds to the patient's arch. There is no need for complex and costly units such as micro-actuators for adjusting multiple degrees of freedom for each tooth model. The described methods and system is simple to make and easy to use.

The physical dental arch model obtained by the disclosed system and methods can be used for various dental applications such as dental crown, dental bridge, aligner fabrication, biometrics, and teeth whitening. The arch model can be assembled from segmented manufacturable components that can be individually manufactured by automated, precise numerical manufacturing techniques.

Yet another advantageous feature of the disclosed system and methods is that the physical tooth models in the physical dental arch model can be easily separated, repaired or replaced, and reassembled after the assembly without the replacement of the whole arch model.

The details of one or more embodiments are set forth in the accompanying drawing and in the description below. Other features, objects, and advantages of the system will become apparent from the description and drawings, and from the claims.

BRIEF DESCRIPTION OF THE DRAWINGS

The accompanying drawing, which are incorporated in and form a part of this specification, illustrate embodiments of the system and, together with the description, serve to explain the principles of the system.

DESCRIPTION OF INVENTION

Figure 1:
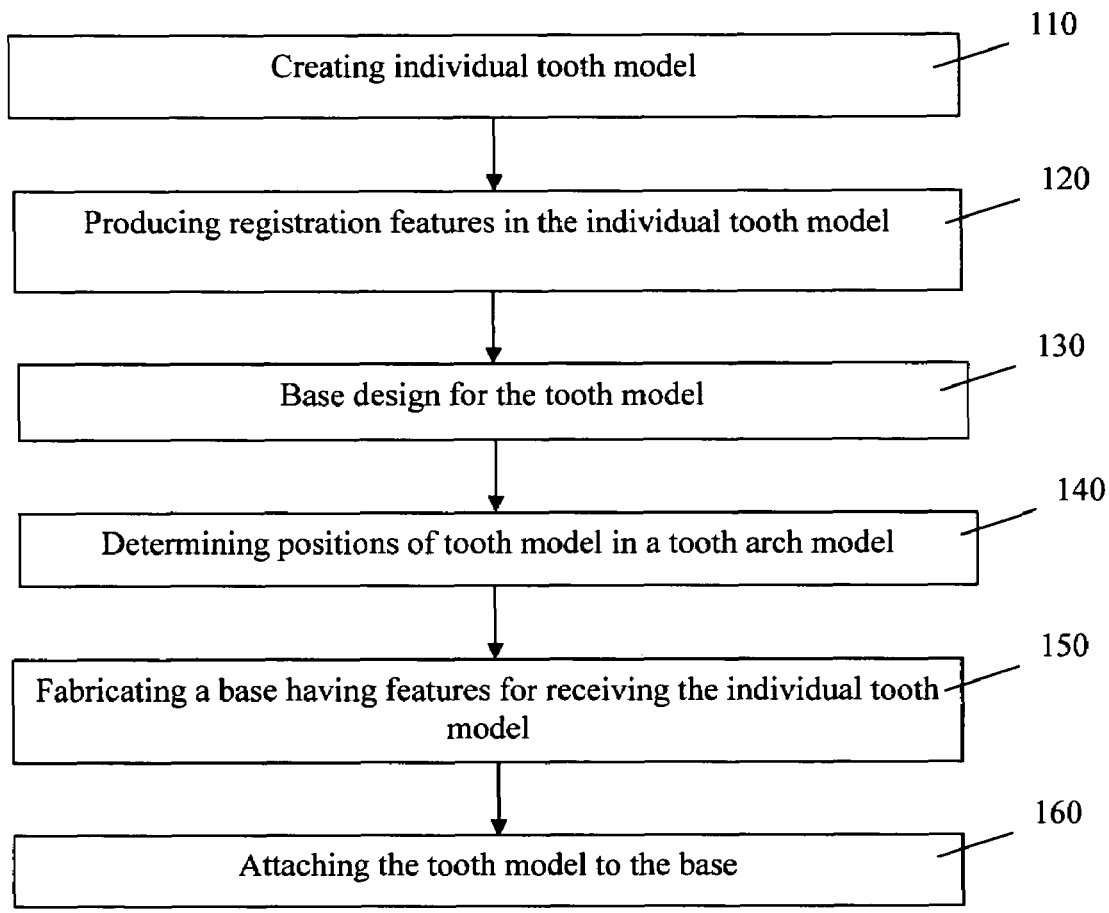
FIG. 1 is a flow chart for producing a physical dental arch model in accordance with the present system.

Major operations in producing a physical dental arch model are illustrated in FIG. 1. The process generally includes the following steps. First individual tooth model is created in step 110. An individual tooth model is a physical model that can be part of a physical tooth arch model, which can be used in various dental applications. Registration features are next added to the individual tooth model to allow them to be attached to each other or a base in step 120. A base is designed for receiving the tooth model in step 130. The tooth model positions in a tooth arch model are next determined in step 140. A base is fabricated in step 150. The base includes features for receiving the individual tooth model. The tooth models are finally attached to the base at the pre-determined positions using the pre-designed features in step 160.

Details of process in FIG. 1 are now described. Individual tooth models can be obtained in step 110 in a number of different methods. The tooth model can be created by casting. A negative impression is first made from a patient's arch or a patient's tooth using for example PVS. The negative impression of the patient's arch is placed in a specially designed chamber. A casting material is then poured into the chamber over the impression to create a model. A lid is subsequently placed over the chamber. The chamber is opened and the mould can be removed after the specified time.

Examples of casting materials include auto polymerizing acrylic resin, thermoplastic resin, light-polymerized acrylic resins, polymerizing silicone, polyether, plaster, epoxies, or a mixture of materials. The casting material is selected based on the uses of the cast. The material should be easy for cutting to obtain individual tooth model. Additionally, the material needs to be strong enough for the tooth model to take the pressure in pressure form for producing a dental aligner. Details of making a dental aligner are disclosed in commonly assigned and above referenced U.S. patent application titled "Method and apparatus for manufacturing and constructing a dental aligner" by Huafeng Wen, filed Nov. 1, 2004, the content of which is incorporated herein by reference.

Figure 10:
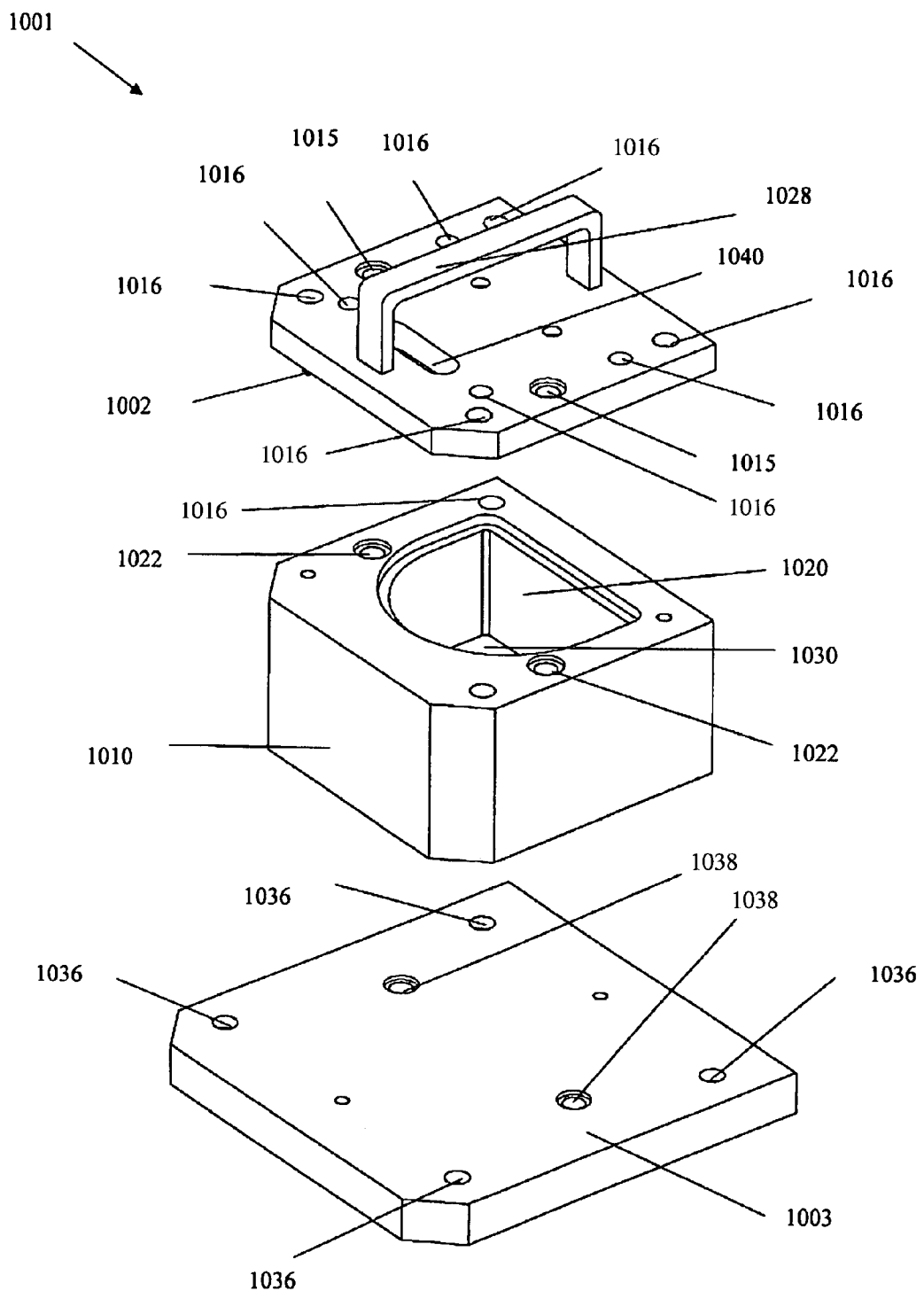
FIG. 10 illustrates an exploded top perspective view of a casting chamber, a chamber lid, and a base for casting a physical tooth model.
Figure 11:
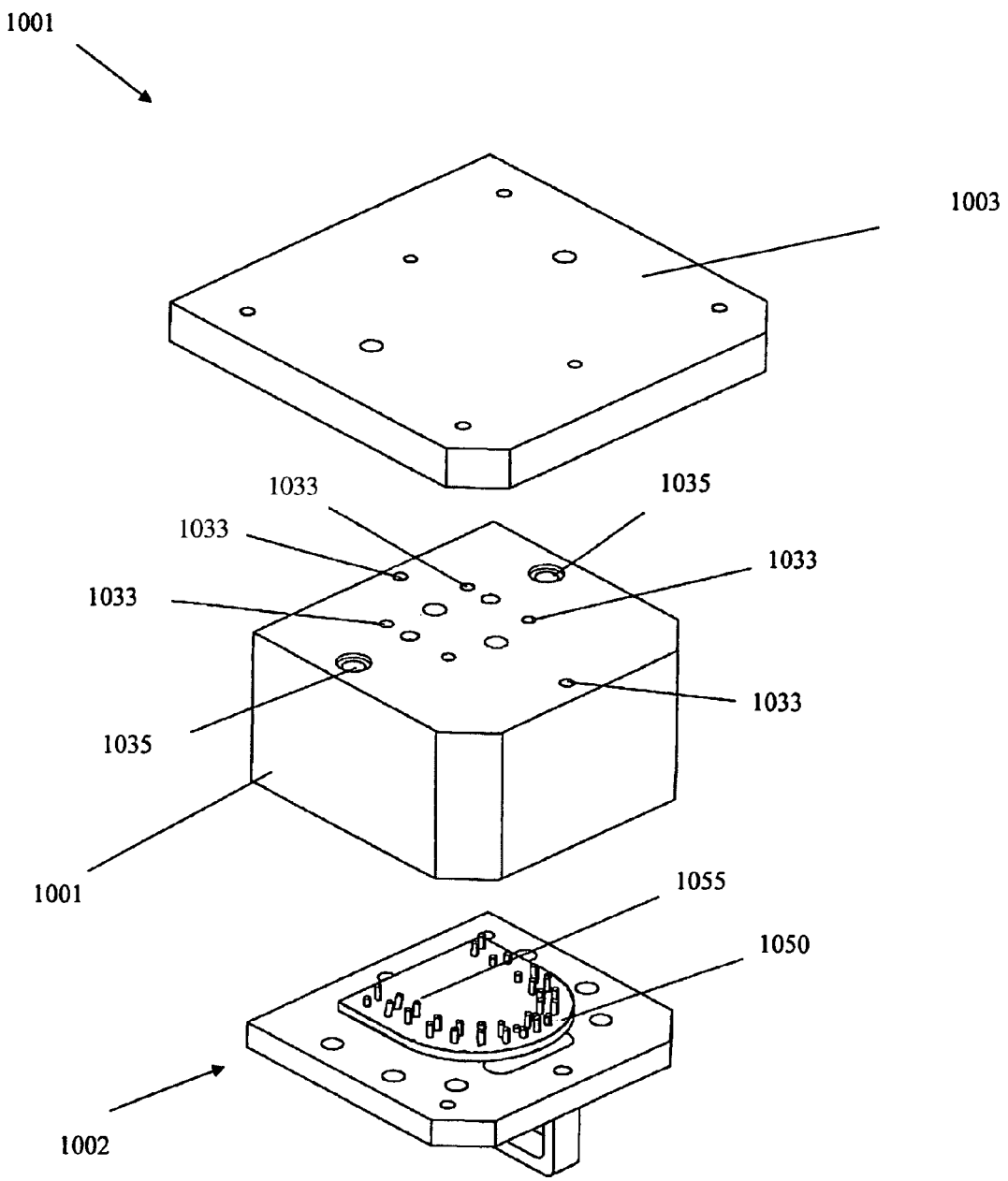
FIG. 11 illustrates an exploded bottom perspective view of a casting chamber, a chamber lid, and a base for casting a physical tooth model.

FIG. 10 and FIG. 11 respectively illustrate exploded top and bottom perspective views casting chamber 1001 including a chamber body 1010, a chamber lid 1002, and a chamber base 1003 for casting a physical tooth model. Chamber body 1010 assembly includes a cavity 1020 and a mounting plate 1030 inside the chamber cavity 1020.

A negative impression of a patient's tooth or arch can be glued or fastened to the mounting plate 1030. At the bottom surface 1031 of the impression mounting plate 1030, there are two precision alignment liners that mate with two precision locating pins on the chamber cavity 1020 bottom surface. The two precision locating pins and liners allow precise locating of the impression repetitively. Furthermore, multiple through holes 1033 through the bottom of the cast chamber to the cavity 1020 provide access to the impression mount plate to assist the removal of the impression mounting plate 1030 from the cast chamber.

The chamber lid 1002 is mated precisely to the casting chamber body 1010 by two precision locating liners 1015 on the chamber lid 1002 and two precision alignment pins 1055 on the casting chamber assembly top surface. The two precision locating liners 1015 on the chamber lid 1002 and the aligners 1022 on the chamber body 1010 also serve as position references for measurement and machining. These features allow repetitive cast of the teeth with precise locations of the teeth.

On the bottom of the casting chamber 1001, there are two additional precision alignment liners 1035. The two liners register with two precision locating pins on the casting chamber base sub-assembly, which allows precise installation of cast chambers to the chamber base for measurement and machining.

Chamber lid 1002 can include a variable spacer 1050 and a casting adaptor. The thickness of the variable spacer is determined by measuring the height of the impression inside the casting chamber cavity 1020. The maximum thickness of the spacer is used so that the distance of the casting adaptor and the impression is minimum when the lid 1002 is tightly placed on the casting chamber body 1010. To achieve the minimum distance between the casting adaptor and the teeth, the adaptor can have a horse-shoe-shaped extrusion machined out of plastics or metal parts.

The casting adaptor is a machined part. Measurements of the specific teeth impression are used to calculate the required machine operations. There are multiple undersized holes on the adaptor to hold the metal pins tightly during the casting process. The locations and orientations of the pins are calculated from measurements of the impression inside the cavity 1020 of the chamber body 1010. In some cases, a horse-shoe-shaped extrusion step is also machined based on specific measurement.

The casting chamber lid 1002 includes multiple threaded through holes 1016 around the cavity 1020 of the casting chamber 1001. These holes serve as a lifting unit to overcome the large forces involved in de-molding. Metal bolts or screws are pushed through the threaded holes to lift the chamber lid 1002 and the cured mold out of the impression.

A plurality of through holes on the casting chamber lid 1002 allows the fastening of the chamber lid 1002 to the Chamber body 1010 during the cast and cure process. The chamber lid 1002 is fixed tightly to the casting Chamber body 1010, maintaining the precision locations during processes such as vibrating, elevated temperature cure process as well as transportation during the cure process.

The casting chamber lid 1002 also has a slotted through window 1040. This window acts a view port as well as an overflow reservoir for the plastics liquid. The chamber lid 1002 also includes a handle 1028 for easy carrying and handling of the chamber lid 1002. In another embodiment, the window allows UV light irradiation through the window to assist the polymerization and solidification of the casting material in the casting chamber 1001. The cast material can be solidified by cooling or heating, irradiation by UV or IR light, or by microwave radiation. The cast material can comprise one or more crosslinking agents that can cause the polymerization and solidification of the cast material to produce the physical tooth model.

Chamber base 1003 is normally fixed to a platform using the multiple through holes 1036. The platform can also host measurement devices. The two precision locating pins on the chamber body 1010 with the two precision liners 1038 on the bottom of a chamber body 1010, thus produce repetitively precision mount of the casting chambers 1001 on to the chamber base 1003.

A feature of the disclosed casting system is the uses of precision locating pins and liners in the casting chamber 1001, the chamber lid 1002 and the chamber base. Precision measurement and computer software can also be used to produce the positions of the receiving features of the physical tooth model. The receiving features enable the physical tooth mode to be mounted or attached to a physical base. The receiving features can include a pin, a registration slot, a socket, a notch, a protrusion, a hole, an interlocking mechanism, a jig, and a pluggable or attachable feature. The physical base as shown in FIGS. 2-9 include complimentary second features for receiving the first features to enable the physical tooth models to be mounted to the physical base. The precise positions of the first features are used for determining the locations of the second features in the physical base in fabricating the base.

In accordance with the present system, the precision units in the casting chamber design are also used in other manufacturing processes such as 2D scanning, base plate machining, and bite setting measurement. 2D scanning is a manufacturing process where an impression for a patient's teeth are measured for the positions and orientations of the simulated "roots"—the metal pins. A measurement device such as a digitizer is mounted rigidly on a flat platform. Multiple pairs of precision locating pins on the platform can receive the mating precision liners on the bottom of the casting chamber 1001. The locating pins positions relative to the measurement device are precisely machined and measured, providing position references for the measurements. The measurement device must have the capabilities of measuring 5-degree of freedoms at each reading in order to provide accurate and efficient measurements.

After a casting chamber 1001 is placed on top of this measurement platform, the chamber can be fixed or clamped down tightly with fasteners through the mounting holes on the casting chamber 1001. The measurement device such as a digitizer is first calibrated against the particular chamber, by measuring the locations of two precision locating pins at the top of the surface. After calibration, the locations and orientations of each tooth are measured. More than two points for each tooth are measured. The gingival shape is also measured. Other measurements include the height of the impression, etc. These positions and orientation data is stored in a computer to be used for future treatment and manufacturing processes.

Bite setting positions of the upper teeth and lower teeth of a patient can also be measured using references to the precision locating liners on the casting chamber lid. After both the lower teeth and the upper teeth of a patient are cast, and de-molded. The two chamber lids with the upper teeth and the lower teeth are set to their nature bite setting position. Springs and universal joints can be used to hold the upper and lower teeth with chamber lids in the bite setting position. A measurement device is then used to measure the relationships between the pair of the precision locating liners on both chamber lids. With the assistance of known positions of the teeth to each chamber lids that are measured and calculated during the machining of the base plate, the nature bite position of the upper and lower teeth are then calculated.

Features that enable tooth models to be attached to a base (step 120) can be added to the casting material in the casting process. Registration points or pins can be added to each tooth before the casting material is dried. Optionally, universal joints can be inserted at the top of the casting chamber 1001 using specially designed lids, which would hang the universal joints directly into the casting area for each tooth.

Still in step 110, individual tooth models are next cut from the arch positive. One requirement for cutting is to obtain individual teeth in such a manner that they can be joined again to form a tooth arch. The separation of individual teeth from the mould can be achieved using a number of different cutting methods including laser cutting and mechanical sawing.

Separating the positive mould of the arch into tooth models may result in the loss of the relative 3D coordinates of the individual tooth models in an arch. Several methods are provided in step 120 for finding relative position of the tooth models. In one embodiment, unique registration features are added to each pair of tooth models before the positive arch mould is separated. The separated tooth models can be assembled to form a physical dental arch model by matching tooth models having the same unique registration marks.

The positive arch mould can also be digitized by a three-dimensional scanning using a technique such as laser scanning, optical scanning, destructive scanning, CT scanning and Sound Wave Scanning. A physical digital arch model is therefore obtained. The physical digital arch model is subsequently smoothened and segmented. Each segment can be physically fabricated by CNC based manufacturing to obtain individual tooth models. The physical digital arch model tracks and stores the positions of the individual tooth models. Unique registration marks can be added to the digital tooth models that can be made into a physical feature in CNC base manufacturing.

Examples of CNC based manufacturing include CNC based milling, Stereolithography, Laminated Object Manufacturing, Selective Laser Sintering, Fused Deposition Modeling, Solid Ground Curing, and 3D ink jet printing. Details of fabricating tooth models are disclosed in commonly assigned and above referenced U.S. patent application titled "Method and apparatus for manufacturing and constructing a physical dental arch mode" by Huafeng Wen, filed Nov. 1, 2004, the content of which is incorporated herein by reference.

In another embodiment, the separated tooth models are assembled by geometry matching. The intact positive arch impression is first scanned to obtain a 3D physical digital arch model. Individual teeth are then scanned to obtain digital tooth models for individual teeth. The digital tooth models can be matched using rigid body transformations to match a physical digital arch model. Due to complex shape of the arch, inter-proximal areas, root of the teeth and gingival areas may be ignored in the geometry match. High precision is required for matching features such as cusps, points, crevasses, the front faces and back faces of the teeth. Each tooth is sequentially matched to result in rigid body transformations corresponding to the tooth positions that can reconstruct an arch.

In another embodiment, the separated tooth models are assembled and registered with the assistance of a 3D point picking devices. The coordinates of the tooth models are picked up by 3D point picking devices such as stylus or Microscribe devices before separation. Unique registration marks can be added on each tooth model in an arch before separation. The tooth models and the registration marks can be labeled by unique IDs. The tooth arch can later be assembled by identifying tooth models having the same registration marks as were picked from the Jaw. 3D point picking devices can be used to pick the same points again for each tooth model to confirm the tooth coordinates.

The base is designed in step 130 to receive the tooth models. The base and tooth models include complimentary features to allow them to be assembled together. The tooth model has a protruding structure attached to it. The features at the base and tooth models can also include a registration slot, a socket, a notch, a protrusion, a hole, an interlocking mechanism, and a jig. The protruding structure can be obtained during the casting process or be created after casting by using a CNC machine on each tooth. The positions of the receiving features in the base are determined by either the initial positions of the teeth in an arch or the desired teeth positions during a treatment process (step 140).

Figure 2:
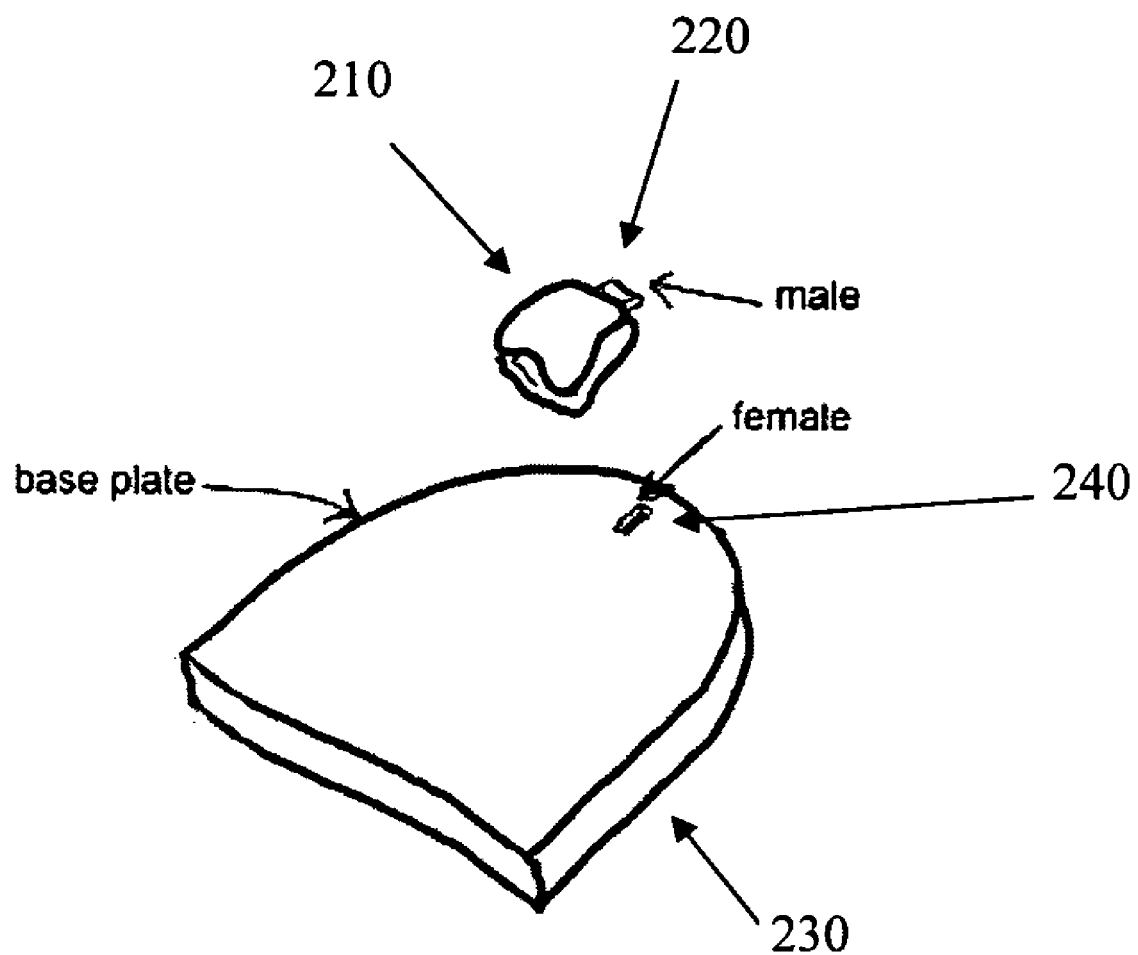
FIG. 2 illustrates a tooth model and a base respectively comprising complimentary features for assembling the tooth model with the base.

Before casting the arch from the impression, the base plate is taken through a CNC process to create the female structures for each individual tooth (step 150). Then the base is placed over the casting chamber in which the impression is already present and the chamber is filled with epoxy. The epoxy gets filled up in the female structures and the resulting mould has the male studs present with each tooth model that can be separated afterwards. FIG. 2 shows a tooth model 210 with male stud 220 after mould separation. The base 230 comprises a female feature 240 that can receive the male stud 220 when the tooth model 210 is assembled to the base 230.

Figure 3:
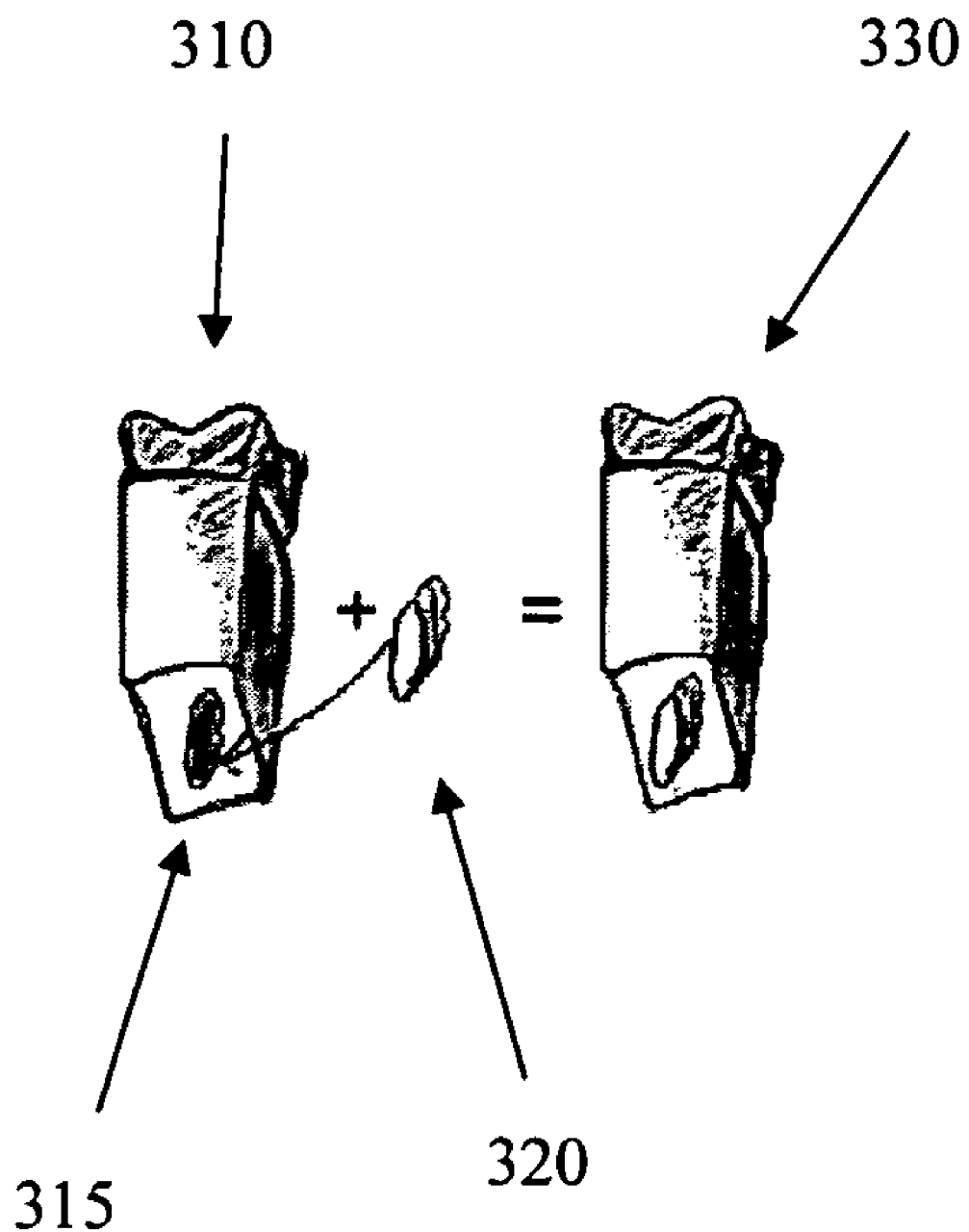
FIG. 3 illustrates fixing a stud to a tooth model comprising a female socket to produce a tooth model having a protruded stud.

Alternatively, as shown in FIG. 3, a tooth model 310 includes a female socket 315 that can be drilled by CNC based machining after casting and separation. A male stud 320 that fits the female socket 315 can be attached to the tooth model 310 by for example, screwing, glue application, etc. The resulted tooth model 330 includes male stud 310 that allows it to be attached to the base.

Figure 4:
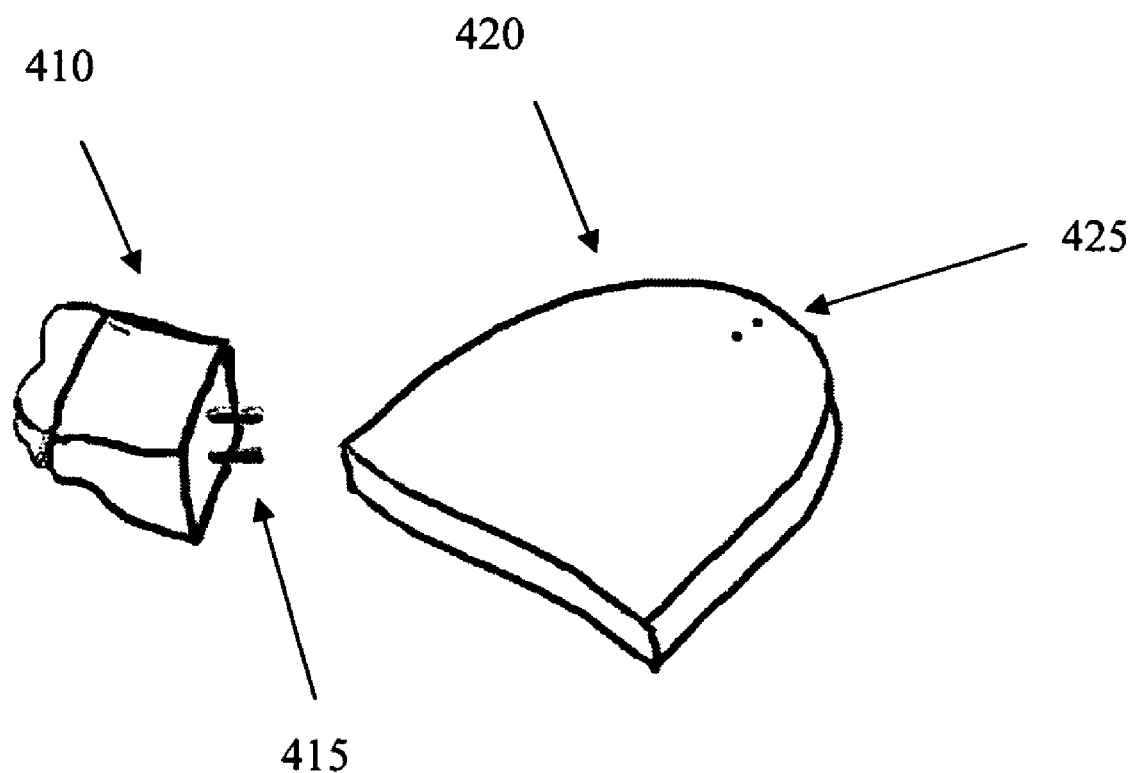
FIG. 4 illustrate a tooth model comprising two pins that allow the tooth model to be plugged into two corresponding holes in a base.
Figure 5:
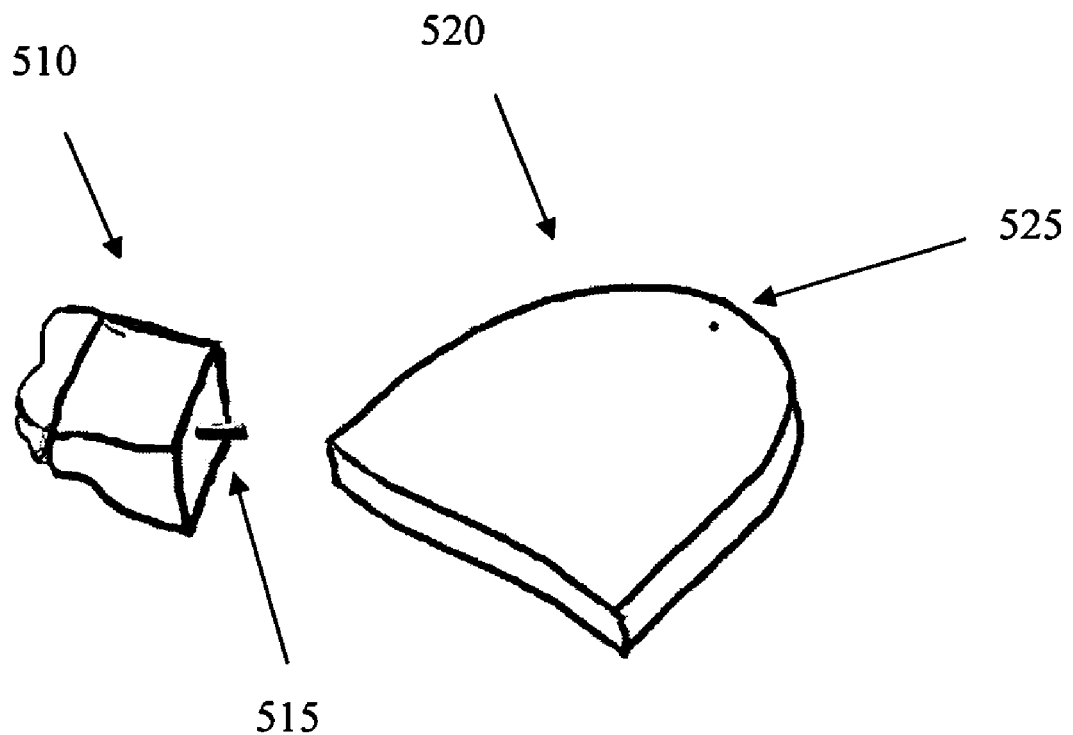
FIG. 5 illustrate a tooth model comprising a protruded pin that allows the tooth model to be plugged into a hole in a base.
Figure 6:
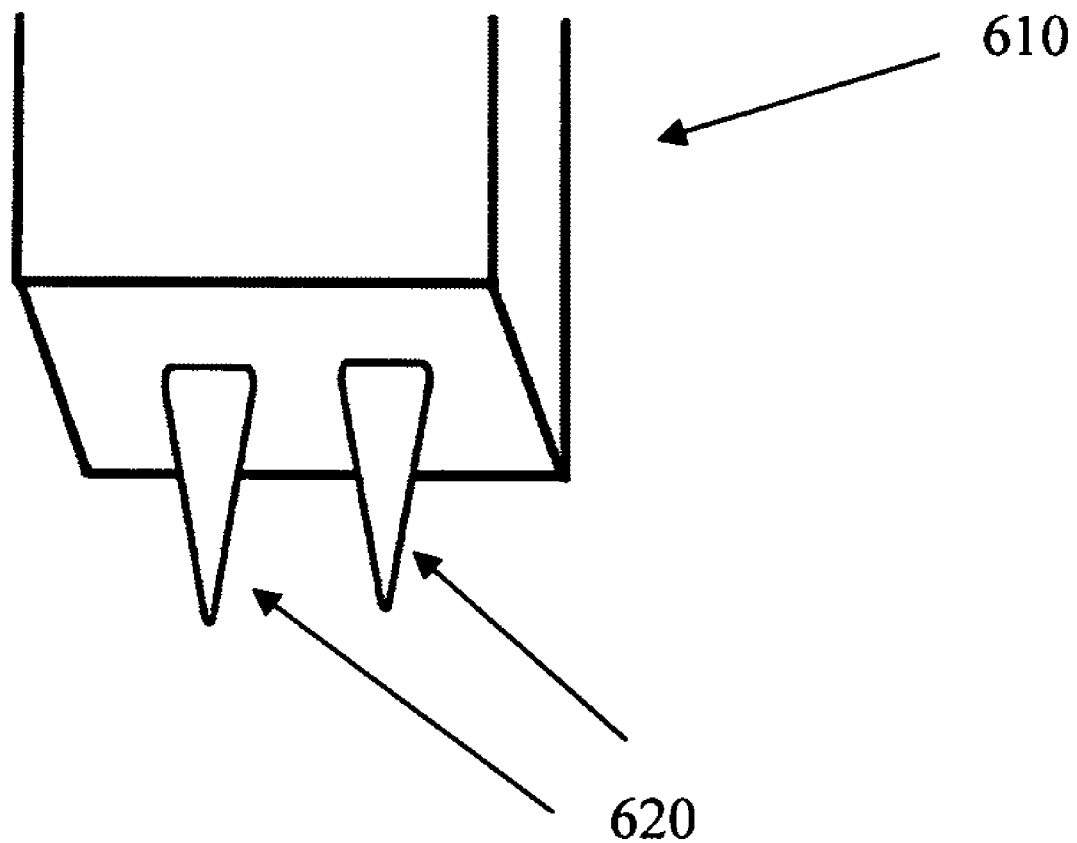
FIG. 6 illustrates cone shaped studs protruded out of the bottom of a tooth model.

Male protrusion features over the tooth model can exist in a number of arrangements. FIG. 4 shows a tooth model 410 having two pins 415 sticking out and a base 420 having registration slots 425 adapted to receive the two pins 415 to allow the tooth model 410 to be attached to the base 420. FIG. 5 shows a tooth model 510 having one pins 515 protruding out and a base 520 having a hole 525 adapted to receive the pin 515 to allow the tooth model 510 to be attached to the base 520. In general, the tooth model can include two or more pins wherein the base will have complementary number of holes at the corresponding locations for each tooth model. The tooth model 610 can also include cone shaped studs 620 as shown in FIG. 6. The studs can also take a combination of configurations described above.

Figure 7:
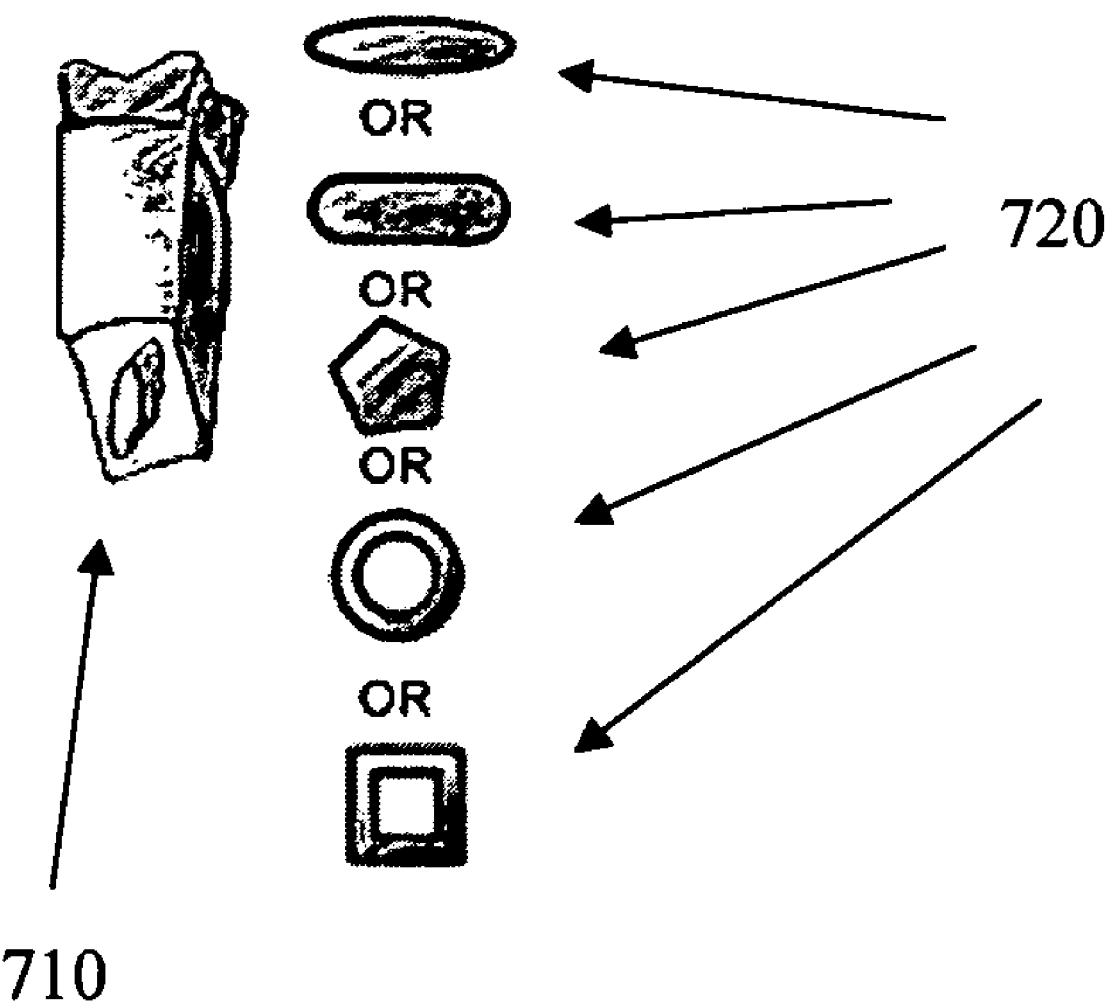
FIG. 7 illustrates exemplified shapes for the studs at the bottom of a tooth model.

As shown FIG. 7, the studs protruding our of the tooth model 710 can take different shapes 720 such as oval, rectangle, square, triangle, circle, semi-circle, each of which correspond to slots on the base having identical shapes that can be drilled using the CNC based machining. The asymmetrically shaped studs can help to define a unique orientation for the tooth model on the base.

Figure 8A:
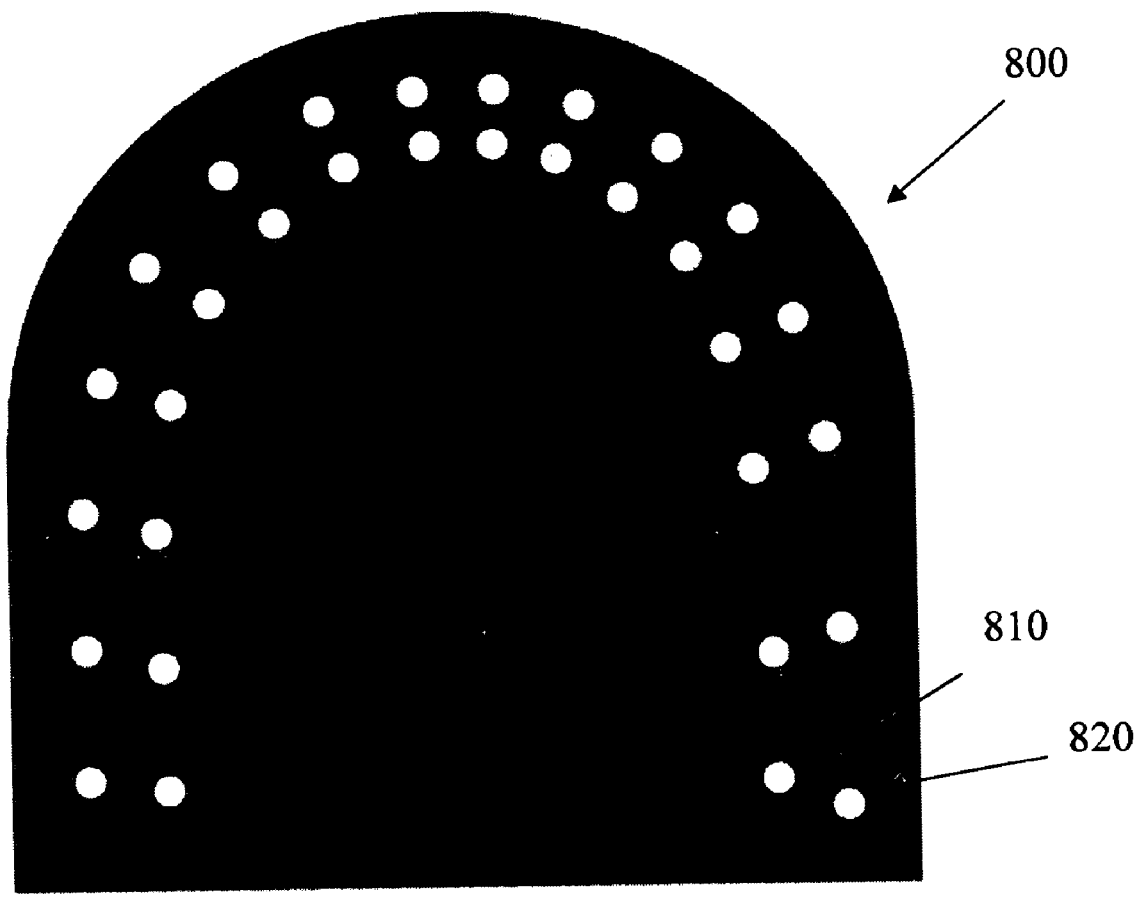
FIG. 8A illustrates an example of a base comprising a plurality of female sockets for receiving a plurality of tooth models for forming a physical dental arch model.

FIG. 8A shows a base 800 having a plurality of sockets 810 and 820 for receiving the studs of a plurality of tooth models. The positions of the sockets 810,820 are determined by either her initial teeth positions in a patient's arch or the teeth positions during the orthodontic treatment process. The base 800 can be in the form of a plate as shown in FIG. 8, comprising a plurality of pairs of sockets 810,820. Each pair of sockets 810,820 is adapted to receive two pins associated with a physical tooth model. Each pair of sockets includes a socket 810 on the inside of the tooth arch model and a socket 820 on the outside of the tooth arch model.

Figure 8B:
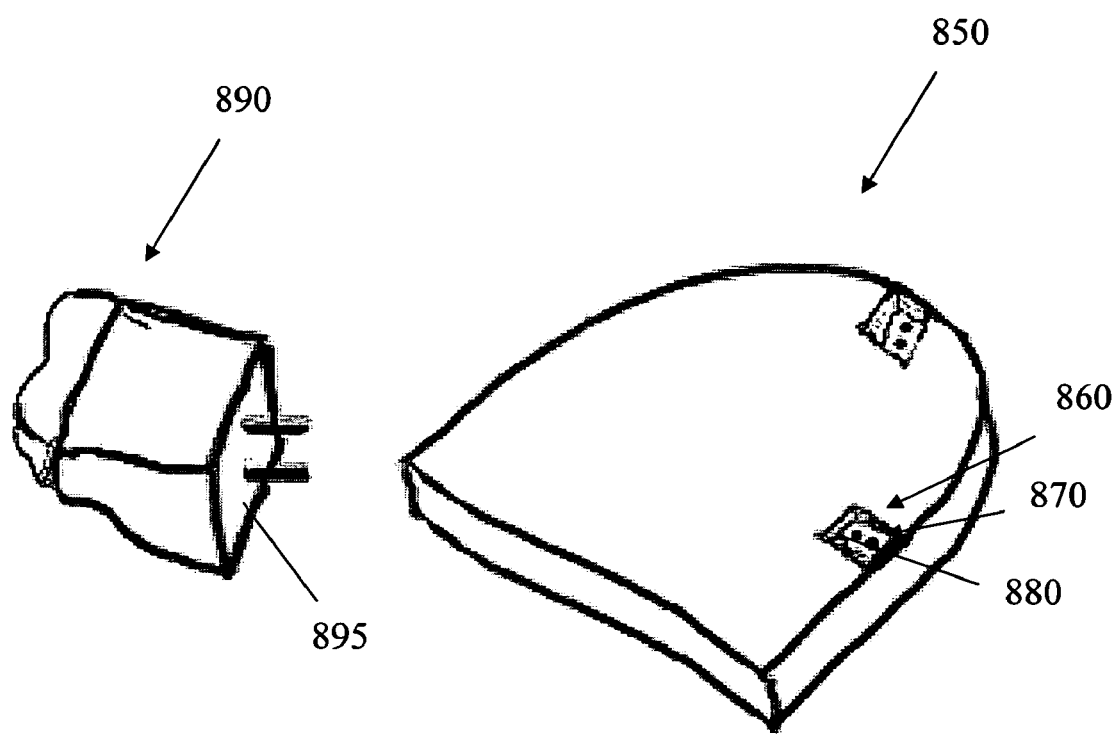
FIG. 8B illustrates another example of a base comprising a plurality of female sockets for receiving a plurality of tooth models for forming a physical dental arch model.

Another of a base 850 is shown in FIG. 8B. A plurality of pairs of female sockets 860, 870 are provided in the base 850. Each pair of the sockets 860, 870 is formed in a surface 880 and is adapted to receive a physical tooth model 890. The bottom portion of the physical tooth model 890 includes a surface 895. The surface 895 comes to contact with the surface 880 when the physical tooth model 890 is inserted into the base 850, which assures the stability of the physical tooth model 890 over the base 850.

Figure 9:
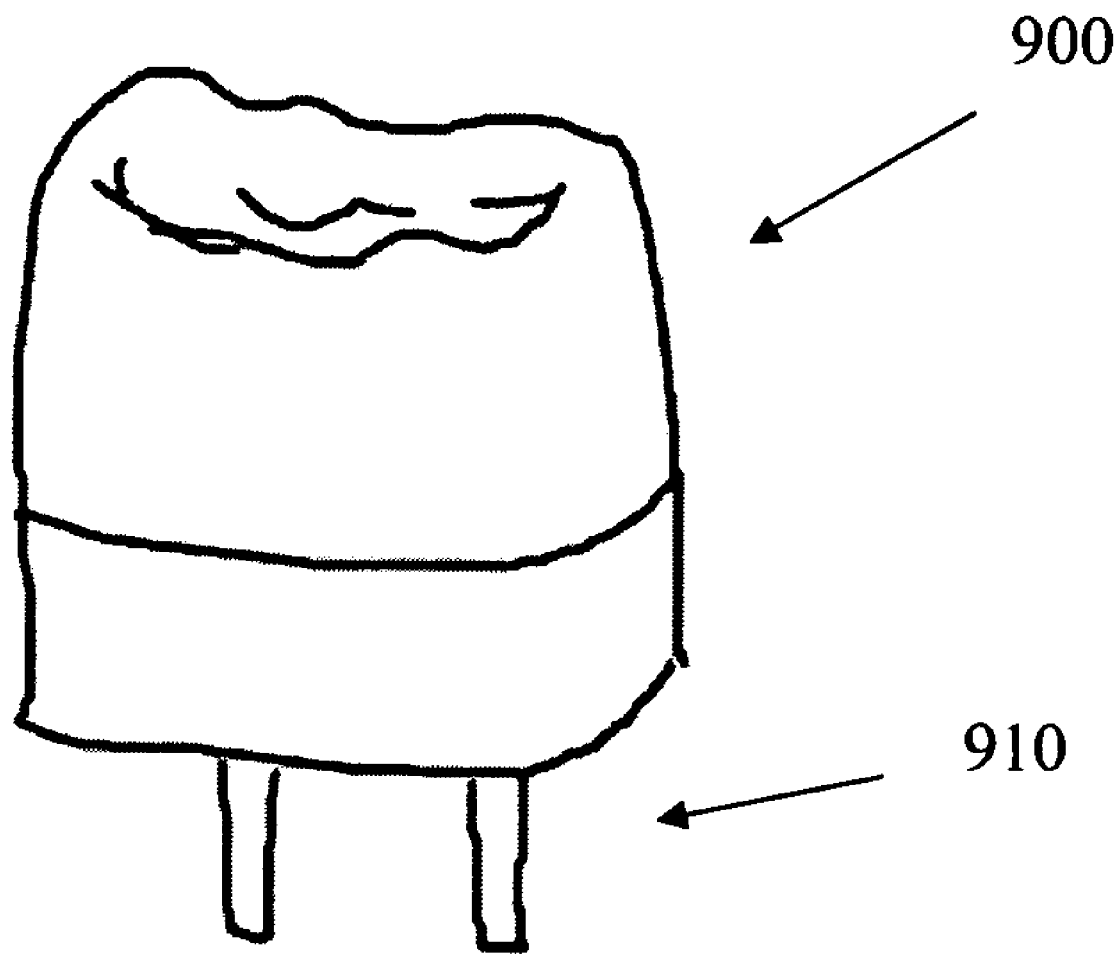
FIG. 9 illustrates a tooth model that can be assembled to the base in FIGS. 8A and 8B.

A tooth model 900 compatible with the base 800 is shown in FIG. 9. The tooth model 900 includes two pins 910 connected to its bottom portion. The two pins 910 can be plugged into a pair of sockets 810 and 820 on the base 800. Thus each pair of sockets 810 and 820 uniquely defines the positions of a tooth model. The orientation of the tooth model is also uniquely defined if the two pins are labeled as inside and outside, or the sockets and the pins are made asymmetric inside and outside. In general, each tooth model may include correspond to one or a plurality of studs that are to be plugged into the corresponding number of sockets. The male studs and the sockets may also take different shapes as described above.

A tooth arch model is obtained after the tooth models are assembled to the base 800 (step 160). The base 800 can comprise a plurality of configurations in the female sockets 810. Each of the configurations is adapted to receive the same physical tooth models to form a different arrangement of at least a portion of a tooth arch model.

The base 800 can be fabricated by a system that includes a computer device adapted to store digital tooth models representing the physical tooth models. As described above, the digital tooth model can be obtained by various scanning techniques. A computer processor can then generate a digital base model compatible with the digital tooth models. An apparatus fabricates the base using CNC based manufacturing in accordance with the digital base model. The base fabricated is adapted to receive the physical tooth models.

The physical tooth models can be labeled by a predetermined sequence that define the positions of the physical tooth models on the base 800. The labels can include a barcode, a printed symbol, hand-written symbol, a Radio Frequency Identification (RFID). The female sockets 810 can also be labeled by the parallel sequence for the physical tooth models.

In one embodiment, tooth models can be separated and repaired after the base. The tooth models can be removed, repaired or replaced, and re-assembled without the replacement of the whole arch model.

Common materials for the tooth models include polymers, urethane, epoxy, plastics, plaster, stone, clay, acrylic, metals, wood, paper, ceramics, and porcelain. The base can comprise a material such as polymers, urethane, epoxy, plastics, plaster, stone, clay, acrylic, metals, wood, paper, ceramics, porcelain, glass, and concrete.

The arch model can be used in different dental applications such as dental crown, dental bridge, aligner fabrication, biometrics, and teeth whitening. For aligner fabrication, for example, each stage of the teeth treatment may correspond a unique physical dental arch model. Aligners can be fabricated using different physical dental arch models one at a time as the teeth movement progresses during the treatment. At each stage of the treatment, the desirable teeth positions for the next stage are calculated. A physical dental arch model having modified teeth positions is fabricated using the process described above. A new aligner is made using the new physical dental arch model.

In accordance with the present system, each base is specific to an arch configuration. There is no need for complex and costly mechanisms such as micro-actuators for adjusting multiple degrees of freedom for each tooth model. The described methods and system is simple to make and easy to use.

The described methods and system are also economic. Different stages of the arch model can share the same tooth models. The positions for the tooth models at each stage of the orthodontic treatment can be modeled using orthodontic treatment software. Each stage of the arch model may use a separate base. Or alternatively, one base can be used in a plurality of stages of the arch models. The base may include a plurality of sets of receptive positions for the tooth models. Each set corresponds to one treatment stage. The tooth models can be reused through the treatment process. Much of the cost of making multiple tooth arch models in orthodontic treatment is therefore eliminated.

Although specific embodiments of the present system have been illustrated in the accompanying drawings and described in the foregoing detailed description, it will be understood that the system is not limited to the particular embodiments described herein, but is capable of numerous rearrangements, modifications, and substitutions without departing from the scope of the system. The following claims are intended to encompass all such modifications.

What is claimed is:

1. A casting chamber to cast a physical tooth model representing a patient's tooth, comprising:
    a chamber body having a cavity adapted to hold a negative impression of the patient's tooth and to receive a cast material, wherein the chamber body comprises a registration unit configured to align the negative impression within the chamber body;
    a chamber lid configured to seal the cast material within the chamber body to permit the cast material to solidify in the chamber body and to form a physical tooth model representing the patient's tooth, wherein the chamber lid is configured to align with the chamber body by the registration unit; and
    the chamber lid comprising a spacer and a casting adaptor, wherein the spacer is configured to minimize the distance between the casting adaptor and the negative impression when the chamber lid is placed on the chamber body.

2. The casting chamber of claim 1, wherein the registration unit includes one or more of a registration pin, a locating pin, an alignment hole, and a liner.

3. The casting chamber of claim 1, further comprising a chamber base coupled to the chamber body.

4. The casting chamber of claim 3, wherein the chamber base is configured to align with the chamber body by the registration unit including one or more of a registration pin, a locating pin, an alignment hole, and a liner.

5. The casting chamber of claim 1, wherein the chamber body comprises one or more chamber walls surrounding the cavity.

6. The casting chamber of claim 5, wherein the chamber walls include one or more through-holes to enable the de-molding of the physical tooth model.

7. The casting chamber of claim 1, further comprising a unit that is configured to assist the solidification of the cast material having been received by the chamber body.

8. The casting chamber of claim 7, wherein the unit provides one or more of cooling, heating, emitting UV light, emitting IR light, and radiating microwave.

9. The casting chamber of claim 7, wherein the unit comprises a window in the chamber lid to permit the irradiation of UV light or IR light through the window to the cast material.

10. A casting chamber to cast a physical tooth model representing a patient's tooth, comprising:
a chamber body having a cavity adapted to hold a negative impression of the patient's tooth and to receive a cast material, wherein the negative impression is registered with the chamber body by a registration unit, and wherein the chamber body comprises one or more chamber walls surrounding the cavity which include one or more through-holes to enable the de-molding of the physical tooth model; and
a chamber lid comprising a spacer and a casting adaptor, wherein the spacer is configured to minimize the distance between the casting adaptor and the negative impression when the chamber lid is placed on the chamber body to seal the cast material in the chamber body and to permit the cast material to solidify in the chamber body and to form a physical tooth model representing the patient's tooth.

11. The casting chamber of claim 10, further comprising a chamber base configured to couple to the chamber body.

12. The casting chamber of claim 11, wherein the chamber base is Configured upon coupling to register with the chamber body by a registration unit including one or more of a registration pin, a locating pin, an alignment hole, and a liner.

13. The casting chamber of claim 10, further comprising a unit that is configured to assist the solidification of the cast material having been received by the chamber body.

14. The casting chamber of claim 13, wherein the unit is configured to provide one or more of cooling, heating, emitting UV light, emitting IR light, and radiating microwave.

15. The casting chamber of claim 13, wherein the unit further comprises a window in the chamber lid to permit the irradiation of UV light or IR light through the window to the casting material.

16. A casting chamber to cast a physical tooth model representing a patient's tooth, comprising:
a chamber body having a cavity adapted to hold a negative impression of the patient's tooth and to receive a cast material, wherein the negative impression and the chamber body are registered by a registration unit;
a chamber lid configured to seal the cast material in the chamber body to permit the cast material to solidify in the casting chamber and to form a physical tooth model representing the patient's tooth, the chamber lid further comprising a spacer and a casting adaptor, wherein the spacer is configured to minimize the distance between the casting adaptor and the negative impression when the chamber lid is placed on the chamber body to; and
a window in the chamber lid to permit the irradiation of UV light or IR light through the window to the casting material.

17. The casting chamber of claim 16, further comprising a chamber base configured to couple to the chamber body.

18. The casting chamber of claim 17, wherein the chamber base upon coupling is registered to the chamber body by a registration unit including one or more of a registration pin, a locating pin, an alignment hole, and a liner.

19. The casting chamber of claim 16, wherein the chamber body comprises one or more chamber walls surrounding the cavity.

20. The casting chamber of claim 16, further comprising a unit that is configured to assist the solidification of the casting material within the casting chamber.

21. The casting chamber of claim 20, wherein the unit provides one or more of cooling, heating, emitting UV light, emitting IR light, and radiating microwave.

22. A method for producing a physical tooth model, comprising:
receiving a negative impression of a patient's tooth in a casting chamber;
machining a casting adapter for coupling to a chamber lid of the casting chamber for minimizing the distance between the negative impression and the chamber lid;
pouring a cast material over the negative impression of the patient's tooth;
sealing the casting chamber with the chamber lid to permit the solidification of the casting material; and
solidifying the cast material to produce the physical tooth model.

23. The method of claim 22, wherein the cast material is selected from the group consisting of polymers, thermal elastic material, urethane, epoxy, plaster, clay, acrylic, latex, dental PVS, resin, metal, aluminum, ice, wax, and one or more crosslinking agents for polymerization.

24. The method of claim 22, further comprising cooling or heating the cast material to cause the solidification of the cast material to produce the physical tooth model.

25. The method of claim 22, further comprising irradiating the cast material with UV light or IR light to cause the solidification of the cast material to produce the physical tooth model.

26. A method for producing a physical tooth model, comprising:
receiving a negative impression of a patient's tooth in a casting chamber;
pouring a cast material over the negative impression of the patient's tooth;
machining a casting adapter for coupling to a chamber lid of the casting chamber for minimizing the distance between the negative impression and the chamber lid; and
irradiating the cast material with UV light or IR light to cause the solidification of the cast material to produce the physical tooth model.

27. The method of claim 26, further comprising sealing the casting chamber by the chamber lid to permit the solidification of the cast material.

28. The method of claim 26, wherein the cast material is selected from the group consisting of polymers, thermal elastic material, urethane, epoxy, plaster, clay, acrylic, latex, dental PVS, resin, metal, aluminum, ice, wax, and one or more crosslinking agents for polymerization.

29. The method of claim 26, further comprising cooling or heating the cast material to cause the solidification of the cast material to produce the physical tooth model.

* * * * *